United States Patent [19]

Goel

[11] Patent Number: 4,788,328

[45] Date of Patent: Nov. 29, 1988

[54] HYDROXY ALKYL (AMINO) ACRYLATE MONOMERS AND COPOLYMERS THEREOF

[75] Inventor: Anil B. Goel, Worthington, Ohio

[73] Assignee: Ashland Oil, Inc., Ashland, Ky.

[21] Appl. No.: 882,330

[22] Filed: Jul. 7, 1986

[51] Int. Cl.⁴ .................................................. C07C 69/52
[52] U.S. Cl. ................................................... 560/222
[58] Field of Search ........................................ 560/222

[56] References Cited

U.S. PATENT DOCUMENTS 4,277,319  7/1981  Nyl et al. ............................ 560/222
4,596,853  6/1986  Goel et al. .......................... 525/398

OTHER PUBLICATIONS

Feinauer, R. Angew. Chem. vol. 79 (1967) 189.
Kirk-Othmer *Encyclopedia of Chemical Technology* 2nd Ed. vol/1, pp. 107–109.

*Primary Examiner*—Paul J. Killos
*Attorney, Agent, or Firm*—John F. Jones

[57] ABSTRACT

The process for preparing novel compounds having the formula

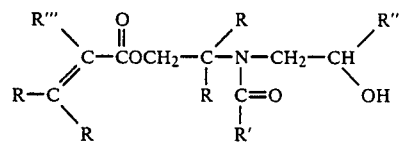

by the reaction of a bicyclic amide acetal of formula

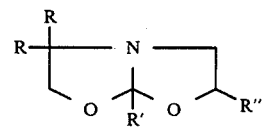

and an olefinically unsaturated carboxylic acid of formula

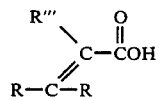

wherein R, R', R" and R'" independently represent hydrogen, an alkyl group or an alkyl ether group having from 1 to 20 carbon atoms, an aryl group or an aryl ether group having from 6 to 12 carbon atoms is described.

4 Claims, No Drawings

HYDROXY ALKYL (AMINO) ACRYLATE MONOMERS AND COPOLYMERS THEREOF

This invention relates a process for preparing novel hydroxy alkyl(amido)acrylate and methacrylate monomers, to the novel monomers themselves and to polymers thereof and more particularly pertains to a process involving the reaction of an olefinically unsaturated carboxylic acid, such as acrylic acid, with a bicyclic amide acetal to form a hydroxy alkyl(amido)acrylate monomer and to the monomer itself and polymers prepared therefrom.

Bicyclic amide acetals are known to react with carboxylic acids as disclosed in *Synthesis,* Page 16, 1971 to give the diester product. The preparation of hydroxy alkyl (amido) acrylate and methacrylate monomers by the reaction of acrylic acid or methacrylic acid with a bicyclic amide acetal has not previously been reported.

I have discovered a process for preparing novel hydroxy alkyl(amido)acrylates and methacrylates (Formula III) by the reaction of a bicyclic amide acetal of Formula I with an olefinically unsaturated carboxylic acid of Formula II as shown in the following equation:

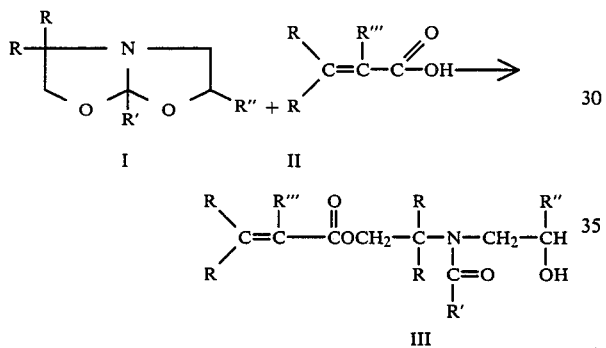

wherein R, R', R" and R'" independently represent hydrogen, an alkyl or alkyl ether group having from 1 to 20 carbon atoms, or an aryl or aryl ether group having from 6 to 12 carbon atoms. I have found that the rate of the foregoing reaction depends largely on the substituents present in the bicyclic amide acetal and for a given unsaturated acid the rate of the reaction follows the trend of: unsubstituted bicyclic amide acetal >monosubstituted bicyclic amide acetal >distribution bicyclic amide acetal >tetrasubstituted bicyclic amide acetal. Thus, for instance, the reaction of methacrylic acid with unsubstituted bicyclic amide acetal (I) (R, R', and R" each represents hydrogen) is so rapid that a neat (solventless) reaction often tends to result in gelation. Similarly, monosubstituted bicyclic amide acetal when reacted with methacrylic acid at room temperature, gels rapidly. On the other hand, the methacrylic acid reaction with disubstituted bicyclic amide acetal proceeds smoothly to give the liquid monomer. Tetrasubstituted bicyclic amide acetals react with methacrylic acid slowly and generally require heat to complete the reaction. The formation of hydroxy alkyl (amido)methacrylates having low substitution from the reaction of monosubstituted bicyclic amide acetal (I) (R and R" represent hydrogen and R' represents an alkyl group) with methacrylic acid may conveniently be carried out in solvents which may include reactive monomers if copolymers are to be made subsequently. The hydroxy alkyl (amido) methacrylates can be prepared in situ in monomers such as methyl methacrylate, styrene, ethyl acrylate, butyl acrylate, and the like and can be copolymerized to give new copolymers after the monomer preparation is completed. Similarly, the hydroxy group of the hydroxy alkyl (amido) methacrylates can be caused to react with polyisocyanates to give unsaturated polyurethane polymers and the olefinically unsaturated moiety of the monomer can also be polymerized by vinyl polymerization either simultaneously or sequentially. Two moles of monomer III can be coupled with diisocyanate to give a diunsaturated monomer (diacrylate) which can be used as a crosslinker in vinyl monomer free radical type addition polymerization.

The process for preparing the hydroxy alkyl(amido) acrylates of this invention may be carried out at a temperature in the range of from about 0° C. to about 100° C. using a ratio of bicyclic amide acetal to acrylic or methacrylic acid in the range of from about 1:0.9 to about 0.9:I (molar) and preferably about 1:1.

In the polymerization or copolymerization of the hydroxy alkyl(amido)acrylate monomers of this invention any free radical initiator known to those skilled in the art can be used such as peroxides, azo compounds, hydroperoxides, radiation, including ultraviolet, nuclear and X-ray types of radiation and even by heat alone. Specific initiators which can be used include t-butyl perbenzoate, t-butyl peroctoate, benzoyl peroxide, cumenehydroyperoxide, azobisisobutyronitrile and by anionic and cationic catalysts as is known in the art and the like and others.

This invention is further illustrated in the following representative examples.

EXAMPLE 1

To 6.4 g of bicyclic amide acetal of Formula I wherein R represents hydrogen, R' represents an ethyl group and R' represents $CH_2OCH_2CH=CH_2$ was added 2.6g of methacrylic acid at room temperature. An exotherm was observed, however, the GLC analysis of a small portion of the product after silylation with bis (trimethylsilyl) trifluoracetamide to block the unreacted methacrylic acid showed the presence of almost all of the starting materials. Thus the exotherm was probably caused by the acid-base salt formation. The reaction mixture was then heated under nitrogen at about 60° C. with stirring and it appeared by periodic sampling and analysis that the reaction reached completion in about 16 minutes yielding product III where R is hydrogen, R' is an ethyl group R'" is $CH_2OCH_2CH=CH_2$ and R"" is a methyl group. The infrared spectrum of the product showed bands at 3370 cm$^{-1}$ (Hydroxyl group), 1720 cm$^{-1}$ (ester group), 1630 cm$^{-1}$ (amide group) showing the presence of product III.

EXAMPLE 2

The procedure of Example 1 was followed using 6.4 g of the bicyclic amide acetal described in Example 1 and 2.6 g of methacrylic acid. The resulting product was mixed with 9 g of styrene and 0.05 g of t-butyl perbenzoate. The solution which resulted was heated slowly and the temperature was raised to about 120° C. Polymerization occurred to give a solid transparent polymer. The polymer was postcured at 120°-130° C. for one hour and the solid was found to be insoluble in toluene and tetrahydrofuran (THF). The Tg (softening point) for the polymer was determined to be 83° C. by differential scanning calorimetry (DSC).

EXAMPLE 3

The procedure of Example 1 was followed using 12.9 g of a bicyclic amide acetal of Formula I wherein R and R'' are hydrogen and R' is a methyl group and 8.5 g of methacrylic acid. An immediate, highly exothermic reaction occurred at room temperature to give a gelled mass suggesting the polymerization of the product III (R and R'' are hydrogen and R' and R''' are methyl).

EXAMPLE 4

To a 250 ml three-neck flask equipped with a stirrer, a thermometer, a water cooled condenser and a dropping funnel was added 20.8 g of styrene, 17.2 g of methacrylic acid and 0.02 g of p-methoxyphenol (polymerization inhibitor). To this was then added dropwise 27.1 g of a bicyclic amide acetal of Formula I wherein R and R'' are hydrogen and R' is methyl and the reaction temperature was maintained at about 24° C. using an ice water bath for control. The reaction was continued for one hour and the resulting solution was analyzed by GLC which indicated almost complete reaction. The infrared spectrum of the product showed bands at 3350 cm$^{-1}$ (hydroxy group), 1720 cm$^{-1}$ (ester carboxyl group) and 1630 cm$^{-1}$ (amide group). To this solution was added 0.2 g of t-butylperbenzoate and the resulting solution was heated at 120° C. Polymerization occurred to give a solid transparent polymer. The Tg (DSC) of the polymer product was found to be 78° C.

EXAMPLE 5

The procedure of Example 4 was followed using 20 g of methyl methacrylate as solvent, 7.2 g of methacrylic acid and 27.'g of the bicyclic amide acetal. The resulting mixture containing the product III in methyl methacrylate solution 1720 cm$^{-1}$ and 1630 cm$^{-1}$. showed infrared bands at 3362 cm$^{-1}$, The resulting mixture was then subjected to polymerization. The clear, transparent solid polymer which resulted was found to have a Tg of 73.3° C. by DSC and a thermal decomposition point in nitrogen of 300° C.

EXAMPLE 6

To a solution of 37 g of dipropylene glycol and 8.6 g of methacrylic acid was added 3.5 g of a bicyclic amide acetal of Formula I wherein R and R'' are hydrogen and R' is a methyl group, and the reaction mixture was stirred at room temperature for one hour. The resulting solution was degassed at reduced pressure and was then mixed with 0.1 g of t-butyl peroctoate, 0.3 g of N,N',N''-tris(dimethylamino propyl) hexahydrotriazine and 92 g of degassed carbodimide modified methylene bis(phenyl isocyanate) (NCO equivalent weight of 144). The resulting solution was poured into a hot mold kept at 100° C. and prepared by using two parallel silicone mold release coated glass plates held apart by ⅛ inch thick spacers. Polymerization occurred rapidly to give a solid polymer sheet which was postcured at 130° C. for 30 minutes. The final polymer sheet was found by analysis to have anotched izod impact strength (ASTM D256) of 0.8 foot pounds/inch of notch and a heat distortion temperature (ASTM D648) of 110° C.

EXAMPLE 7

To a solution of 35 g of butyl acrylate sovent and 5 g of methacrylic acid was added 8 g of a bicyclic amide acetal of Formula I wherein R and R'' are hydrogen and R' is a methyl group. The resulting solution was stirred at room temperature for one hour. To this solution was then added an additional 40 g of the bicyclic amide acetal and 0.2 g of t-butyl peroctoate and this was mixed rapidly with 113 g of modified liquid methylene bis(phenyl isocyanate) (isocyanate functionality of 2.1 NCO per molecule) and the resulting solution was poured into the glass mold described in Example 6. The polymer which resulted after postcuring as described in Example 6 was found to have a notched izod impact strength of 0.9 foot pounds/inch of notch and a heat distortion temperature of 123° C.

I claim:

1. The process comprising reacting at a temperature in the range of from about 0° C. to about 100° C. a bicyclic amide acetal having the formula I

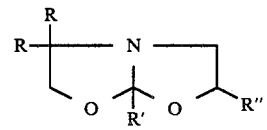

with olefinically unsaturated carboxylic acid having the formula II

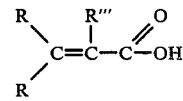

to form a hydroxy alkyl (amido) acrylate monomer having the formula III

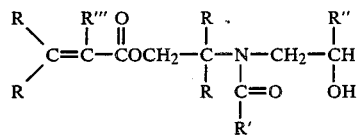

wherein R, R', R'' and R''' independently represent hydrogen, an alkyl group or an alkyl ether group having from 1 to 20 carbon atoms, an aryl group or aryl ether group having from 6 to 12 carbon atoms wherein the molar ratio of bicyclic amide acetal to unsaturated carboxylic acid is in the range of from about 1:0.9 to 0.9:1.

2. The process of claim 1 wherein the olefinically unsaturated carboxylic acid is methacrylic acid.

3. The process of claim 2 wherein the bicyclic amide acetal is one in which R represents hydrogen, R' represents an ethyl group and R'' represents CH$_2$—OCH$_2$—CH=CH$_2$ 4. The process of claim 2 wherein the bicyclic amide acetal is one in which R and R'' represent hydrogen and R' represents a methyl group.

* * * * *